US008979846B2

(12) United States Patent
Thakkar

(10) Patent No.: US 8,979,846 B2
(45) Date of Patent: Mar. 17, 2015

(54) FLEXIBLE NAIL ASSEMBLY FOR FRACTURES OF LONG BONES

(76) Inventor: Navin N Thakkar, Ahmedabad (IN)

(*) Notice: Subject to any disclaimer, the term of this patent is extended or adjusted under 35 U.S.C. 154(b) by 1480 days.

(21) Appl. No.: 10/599,854

(22) PCT Filed: Apr. 7, 2005

(86) PCT No.: PCT/IN2005/000103
§ 371 (c)(1),
(2), (4) Date: Oct. 11, 2006

(87) PCT Pub. No.: WO2005/096976
PCT Pub. Date: Oct. 20, 2005

(65) Prior Publication Data
US 2007/0173834 A1    Jul. 26, 2007

(30) Foreign Application Priority Data
Apr. 12, 2004  (IN) .................. 438/MUM/2004

(51) Int. Cl.
*A61B 17/72*          (2006.01)
(52) U.S. Cl.
CPC ......... *A61B 17/7208* (2013.01); *A61B 17/7283* (2013.01)
USPC .......................................................... 606/62
(58) Field of Classification Search
CPC ............... A61B 17/72; A61B 17/7208; A61B 17/7216; A61B 17/7225
USPC ..................................... 606/62–64
See application file for complete search history.

(56) References Cited

U.S. PATENT DOCUMENTS

| 2,579,968 A | 12/1951 | Rush |
| 2,998,007 A | 8/1961 | Herzog |
| 3,779,239 A | 12/1973 | Fischer et al. |

(Continued)

FOREIGN PATENT DOCUMENTS

| DE | 19707420 | 8/1998 |
| EP | 29752 A1 * | 6/1981 ............. A61B 17/18 |

(Continued)

OTHER PUBLICATIONS

International Search Report for PCT/IN2005/000103, Published by ISA/EP; Dated Sep. 15, 2005. (pp. 1-4).

(Continued)

*Primary Examiner* — Eduardo C Robert
*Assistant Examiner* — Julianna N Harvey

(57) ABSTRACT

An implant assembly of flexible nail for fractures of long bones comprising a straight universal length flexible nail having 15 to 25% of elongation of nail and ultimate tensile strength of 600 to 800 Mega Pascal on testing, wherein flexible nail is having an identical pathfinder blunt conical tip at both ends. An optional proximal fixation device to be used in combination with flexible nails having peripherally spaced plural grooves and optional plural holes for interlocking screws wherein each groove is deep less than diameter of one of flexible nails. An end cap with plural holes to be used in combination with proximal fixation device to anchor cut hooked ends of flexible nails. A tool plier-knurler cum cutter temporarily applied when flexible nails are alone in use.

8 Claims, 11 Drawing Sheets

(56) References Cited

U.S. PATENT DOCUMENTS

| | | | |
|---|---|---|---|
| 4,169,470 A | | 10/1979 | Ender et al. |
| 4,457,301 A | * | 7/1984 | Walker .................. 606/62 |
| 4,467,793 A | * | 8/1984 | Ender .................... 606/62 |
| 4,473,069 A | * | 9/1984 | Kolmert ................. 606/64 |
| 4,712,541 A | | 12/1987 | Harder et al. |
| 5,192,281 A | * | 3/1993 | de la Caffiniere ...... 606/59 |
| 5,281,225 A | * | 1/1994 | Vicenzi .................. 606/62 |
| 5,968,078 A | * | 10/1999 | Grotz .................... 606/232 |
| 5,976,140 A | * | 11/1999 | Haas ..................... 606/328 |
| 6,106,528 A | * | 8/2000 | Durham et al. ......... 606/64 |
| 6,551,321 B1 | | 4/2003 | Burkinshaw et al. |
| 6,783,530 B1 | | 8/2004 | Levy |
| 2002/0143339 A1 | * | 10/2002 | Medoff .................. 606/72 |
| 2004/0167566 A1 | * | 8/2004 | Beulke et al. .......... 606/200 |
| 2004/0230193 A1 | | 11/2004 | Cheung et al. |

FOREIGN PATENT DOCUMENTS

| | | |
|---|---|---|
| EP | 0401650 | 12/1990 |
| EP | WO 98/36699 | 8/1998 |
| FR | 2657005 | 7/1991 |
| FR | 2844701 | 3/2004 |

OTHER PUBLICATIONS

John M. Flynn, Timothy Hresko, Richard A. K. Reynolds, R. Dale Blasier, Richard Davidson and James Kasser "Titanium Elastic Nails for Pediatric Femur Fractures: A Multicenter Study of Early Results with Analysis of Complications" from Journal of Pediatric Orthopaedics, vol. 21, No. 1, Lippincott Williams & Wilkins, Inc., Philadelphia; pp. 1-5; 2001.

* cited by examiner

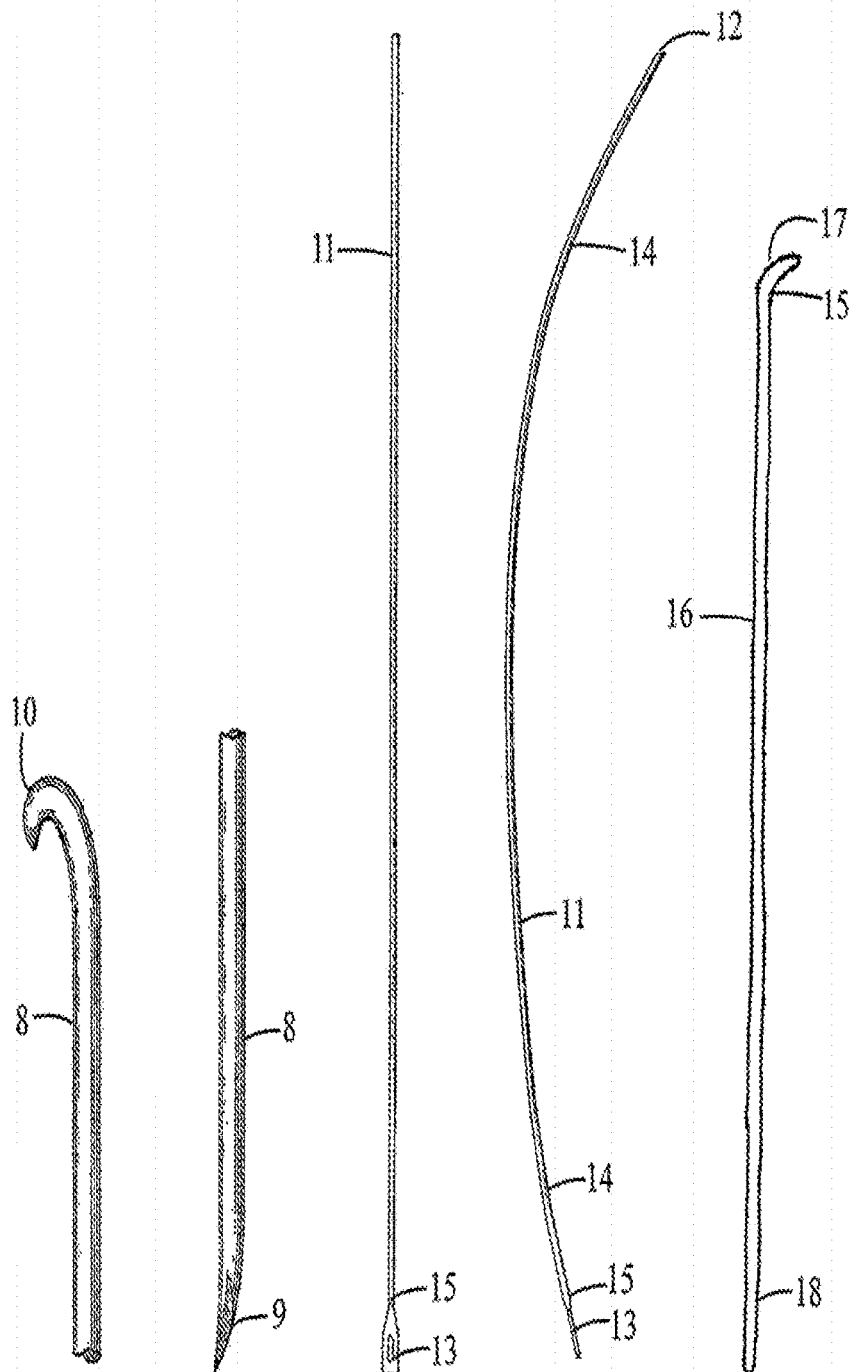

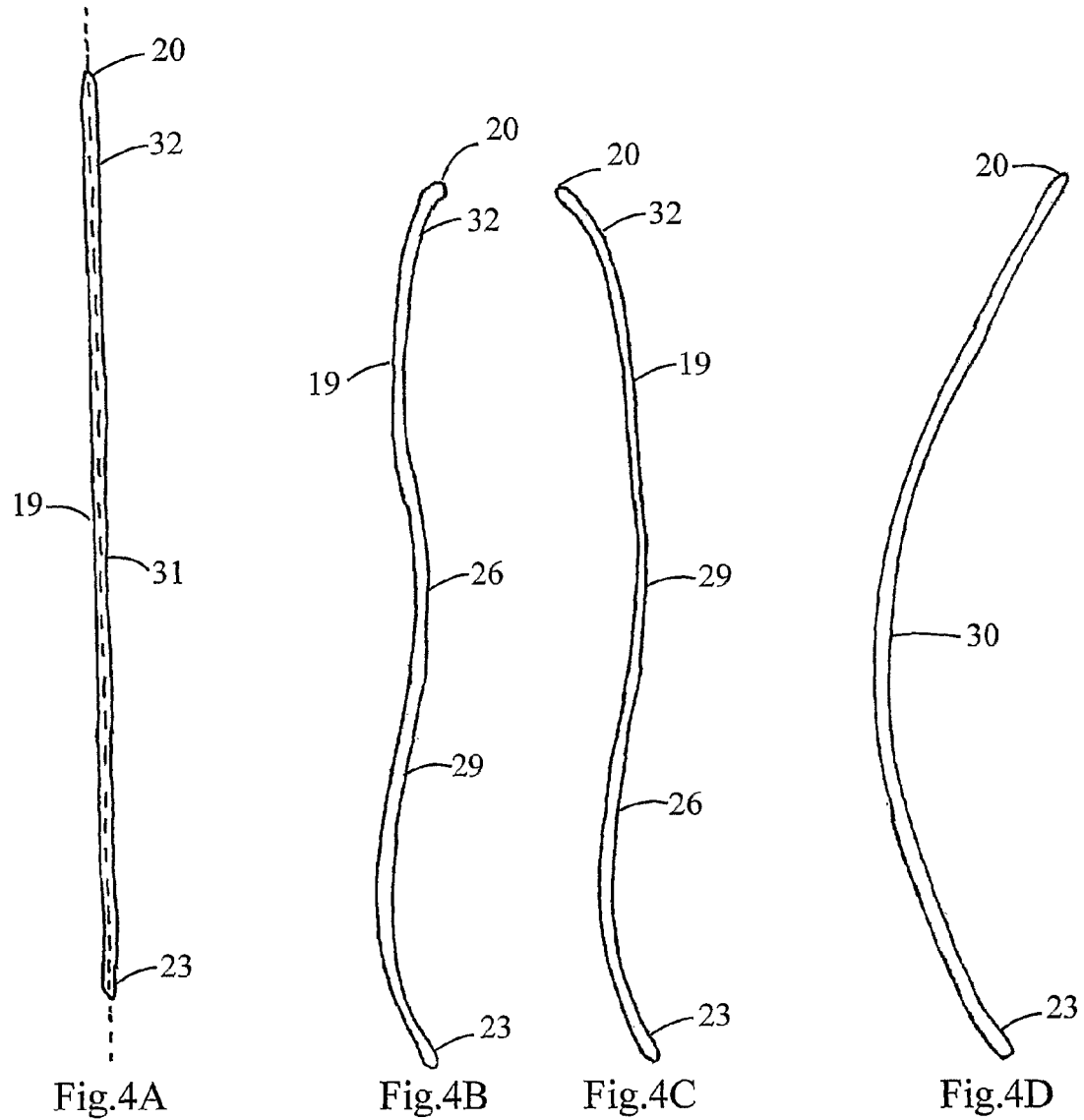

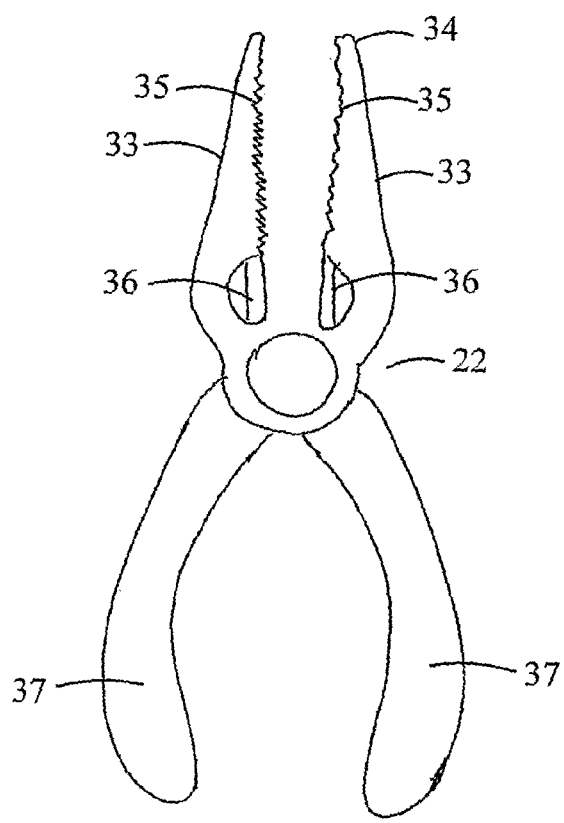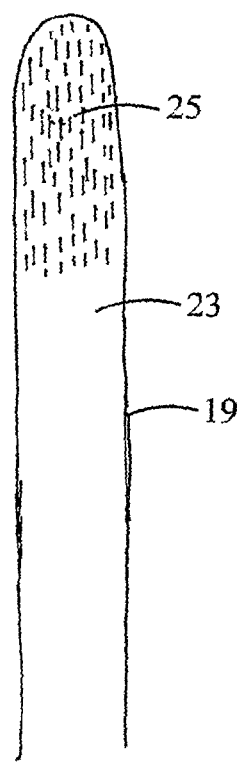
Fig. 6A
Fig. 6B

FLEXIBLE NAIL ASSEMBLY FOR FRACTURES OF LONG BONES

The present application is related to and claims priority from PCT application PCT/IN2005/000103 filed on 7 Apr. 2005, which in turn claims priority from India Patent Application 438/MUM/2004 filed on 12 Apr., 2004, which are both incorporated in their entirety herewith.

TECHNICAL FIELD

The present invention relates to an orthopedic implant assembly used to repair fractures of the long bones particularly in children and in certain conditions in adults by generally more than one flexible intramedullary nails. These nails are having very high flexibility with high tensile strength and gliding conical pathfinder tip at both ends with optional fixation device for retention of flexible nails at one end and having in combination temporarily applied at distal end of nail, a tool like plier-knurler cum cutter to get knurling type effect at cut ends of nails.

BACKGROUND ART

As shown in FIGS. 1 and 2, Long bones of children like femur (1) and tibia (2) are having growing ends—epiphysis (3) having growth plate (4), a nongrowing shaft—diaphysis (5) and intermediate part—metaphysis (6). Injury or irritation to this epiphysis (3) directly or indirectly hampering its blood supply leads to deformity of bone and limb. Treatment of Fractures of long bones of weight bearing lower limb like femur (1)—thigh bone, tibia (2) and fibula—leg bones and non weight bearing upper limb bones like humerus (54)—arm bone, radius (55) and ulna (56)—forearm bones, particularly fractures of shaft or diaphysis (5) many a times require its fixation with nails. To prevent injury to epiphysis (3), entry of such nails required away from the ends of long bone from sides and angled. For such side-angled entry of nails in long bones, require very high flexibility and strength from material of nail. Flexibility of nail is measured indirectly by its ductility, which in turn measured as percentage of elongation of nail during testing of nail on universal testing machine. Strength of nail is measured as stress applied on nail in units of Mega Pascal (MPa) on universal testing machine. Flexibility of nail helps surgeon to have different curves at desired distance and angle to facilitate its introduction in medullary canal (7) and gives multiple point contact to maintain fracture fragments in correct relation during knitting. Long bones of children are elastic and are having different curvatures. Long bones of children are growing, so it requires removal of nails earliest after solid union of fracture.

Experiences of surgeons and clinical studies and mechanical studies have shown that treatment of fractures of long bones by flexible nails require implant assembly with proper biomechanical properties, such as:

It requires high flexibility at the same time high strength to get more curvatures and multiple contact points at medullary canal and due to high flexibility; it should not require two opposite entry sites to balance opposing force of curvatures.

It requires pathfinder-gliding tip to glide in medullary canal, not injuring epiphysis or perforating opposite cortex while making entry in medullary canal.

It should be of universal length to have latitude to surgeon to select any fraction of length suitable for better fixation, at the same time avoid penetration of proximal epiphysis, and avoid irritation of soft tissue at distal end of nail.

It should have facility for surgeon to choose different cross section diameters in combination to get adapted well in any size of medullary canal.

It should have a non leading or projecting end such that it does not irritate soft tissues around it at the same time provide means for easy removal after solid union of fracture without much difficulty.

By having multiple curves and multiple contact interference fit, by rotation of nail it should allow rotational or lateral movement of fracture fragments to improve relation and contact between fragments.

It should allow limited axial loading of fracture fragments without displacement on weight bearing by patient to stimulate bone healing.

It should not back out at knee or non-leading end or penetrate joint on weight bearing by patient.

It should be minimally invasive to patient.

Along with these biomechanical properties, the implant unit should be easy to fix and should provide maximum accuracy of fixation. Therefore, it is adoptable to average surgeon giving reproducible results. It should be cost effective too.

Nails and other devices placed in medulary canal for fractured long bone are in use since long.

Rush, U.S. Pat. No. 2,579,968, Dec. 25, 1951, as shown in FIG. 3A, 3B, discloses a pin (8) of flexible resilient material like stainless steel and which is originally straight except for a slight curve or bend at its forward sharpened end (9). The particular feature taught by the patent resides in the shape of the sharpened distal end, by which that end, in penetrating the medullary canal, is cammed free of the cortex during movement there along. Here, flexibility is less, sharp end does not glide easily in medullary canal, and penetration of opposite cortex of bone is known to occur. Length of pin (8) is not universal. Hooked end (10) can cause irritation.

Herzog U.S. Pat. No. 2,998,007 Aug. 29, 1961, teaches a stiff rigid steel tube open at both ends and pre-shaped if required by the contour of the particular bone to be repaired. The tube has longitudinal slot at spaced locations along its length. Once emplaced, through an incision at the proximal end of the bone, spring wires are pushed into and through the tube and manipulated so that their ends project from appropriate ones of the slots to become anchored in the cancellous. Thus, the patented device is relatively complicated, difficult to install and properly manipulate. Apparently, it immobilizes the patient's joint at the proximal end of the bone.

Another prior art device is shown by Fischer et al., U.S. Pat. No. 3,779,239, Dec. 18, 1973, showing a complicated structure including a rigid tube or sleeve pre-shaped to conform to the normal shape of that particular bone. At its distal end, the tube carries an expansible section. When the tube and its expansion section are driven into the bone canal through an incision at the proximal end thereof, a rod in inserted into and along the tube, then threadedly attached to the terminal expansion section. Turning of the rod further then causes the expansion of the section to anchor the device within the bone. The device thus shown is complicated and expensive. During emplacement lateral thrust engendered by turning of the flexed rod, tends to cause undesirable transverse movement of the fractured parts due to tendency of the tube to shift or turn in and with respect to the medullary canal. The expense and difficulty in storage of the large number of such devices necessary to service any fractured bone of the body, are clear.

Ender et al., U.S. Pat. No. 4,169,470, Oct. 2, 1979, as shown in FIG. 3C, 3D, discloses thin, flexible, elastic, resilient Ender nails (11) pre-shaped for an adult femur curvatures, fixed length from 32 to 49 cm, preferably of diameter of 4.5 mm, having pointed proximal end (12) and flat eye shape (13) at distal end. It is made of metal having elasticity between about 125 Kp/mm.sup.2 to 145 Kp/mm.sup.2 (claim no. 21).

After fixation, it gives three point fixations due to its curvatures (14). After final fixation, with multiple Ender nails (11) at the distal end being flat to permit a fish-scale type-mating overlying with the distal ends of a plurality of other similarly shaped nails when protruding in situ through the incision in the bone. One of the disadvantages is the flattening at the distal end, which are oriented transversely to the axis of curvature. These nails are in addition provided with an aperture for the purpose of obtaining an effective engagement of a drive-in tool, may be effective in the manner of a chisel if they do not come to lie completely flat against the bone and in parallel therewith, respectively. The relatively sharp edges formed in this manner may have an irritating effect on the adjacent tissue. As the flattening is normally formed in an upsetting process, additional processing is required so as to remove any burrs or sharp edges formed in said upsetting step. Through the flattening of a round nail cross sectional area, in addition, a critical zone of transition (15) will form having a relatively high notch effect, so that with a considerable amount of torque applied at the distal end (13) a plastic deformation or even a shearing off may be the result in this zone. Upon rotation of the distal ends (13) against each other, several flattened distal ends require a relatively great amount of space, whereby the well-being of the patient may be affected. Problems with this nails are it is stiffer for use in pediatric long bones, not having enough flexibility leading to straightening of curvatures of bones, pointed end (12) many a times penetrates super-adjacent fracture fragment and penetrate in hip joint (21), which is considered to be a serious complication of the method of treatment rendering it ineffective. On axial loading by weight bearing on limb, due to insufficient ductility or flexibility, it backs out at distal end thereby increases tissue irritation already present at protruding distal end. Other disadvantages are its pre-shaped curvatures not suitable for long bones of children and lesser diameter than 3 mm is routinely required for narrow medullary canals of long bones of children and in certain occasions in adults having poliomyelitis or narrow medullary canal due to other reasons.

Kalmert. U.S. Pat. No. 4,473,069, Sep. 25, 1984, showing similar nails as Ender's nail (11), but it is having a means for prevention of back out of nail, having a separate element, a coupling piece with a plate portion which can be mounted to the outside of the bone by means of one or more cross screws. A coupling hook projects from the plate portion, which forms a cross head and can be brought to engage lockingly the elastic nail by the cross head being passed through a slot in one end of the nail and being rotated. Other disadvantages are same as Ender's patent.

Harder et al. (U.S. Pat. No. 4,712,541, Dec. 15, 187) showing improvisation of Ender's nail (11) by providing a distal end without eye and a proximal end or tip of nail as a rounded-off thickened portion in place of a sharp slanted tip. Other disadvantages are same as Ender's patent.

Walker, U.S. Pat. No. 4,457,301, Jul. 3, 1987, shows an intramedullary bone fracture fixation device comprising a plurality of thin resilient pins substantially longer than the fracture zone to be fixed and a flexible core element holding the pins apart from one another in a desired special arrangement over substantially the full length of the pins. This device with said pins being held in sliding fit in longitudinal grooves in the periphery of said flexible core, wherein the pins are made of titanium alloy Ti-6Al-4V, and the core is made of ultra-high molecular weight polyethylene. Wear of plastic will cause osteolysis. It does not provide any firm anchorage to proximal ends of pins. Due to titanium alloy and ultrahigh molecular weight polyethylene cost of device becomes very high, not affordable to all patients.

Hinze PCT/EP98/01018, Publication No. WO 98/36699, Aug. 27, 1998 shows a fracture nail made of a nickel-titanium alloy which is plastically deformable at a temperature lower than the human body temperature and which returns to its original shape at the body temperature. At the body temperature, the fracture nail has at least one deviation from its straight central axis and at a lower temperature; it can be brought to a substantially straight shape. The fracture nail can thus be firmly braced within the medullary cavity and fully stabilizes the bone. Disadvantages with this nail are it has thermal mechanical-shape memory at particular temperature only, which is difficult to maintain many times during surgery, it has no latitude to surgeon to give desired curvature according to site of fracture. Practically to use this nail is very difficult and due to use of shape memory alloy, cost is high. The ends of nail are sharp pointed. Other examples of use of shape memory alloy are Levy, U.S. Pat. No. 6,783,530, Aug. 31, 2004 and Cheung et al., U.S. Pat. No. 20040230193, Nov. 18, 2004.

Burkinshaw et al., U.S. Pat. No. 6,551,321, Apr. 22, 2003 shows an orthopedic implant including a pair of spaced apart end caps, which are interconnected by a plurality of elongated flexible members. Each end cap includes an aperture formed there through for the use of a trochanteric guide wire for piloting the implant during trial insertion and final insertion into an intramedullary canal. At least one of the end caps includes a rounded end to enhance insertion. Preferably, the flexible members are bowed outwardly to provide a "birdcage" configuration. Disadvantage of this nail is, it is having rigid part at both end secured with flexible part, having flexibility in particular part only, thus not allowing entry point of nail at side and angled to side of long bones of children to prevent injury to epiphysis. It is not having universal length, so requires large inventory of different length and different diameter combination.

Presently used Titanium Elastic Nails (TENs) (16) marketed by Synthes (Paoli, Pa., U.S.A.) are elastic nails made of titanium alloy and recommended for use in fractures of long bones of children. These nails are available in different diameter from 2.5 mm to 4.5 mm, having universal length of 45 cm. As shown in FIG. 3E, it is having a leading or proximal end (17) made flat and bent like hockey stick for entry into medullary canal (7). Distal end (18) is rounded. Through the flattening of a round nail cross sectional area, in addition, a critical zone of transition (15) will form having a relatively high notch effect, so that with a considerable amount of torque applied at the distal end (18), a plastic deformation or even a shearing off may be the result in this zone. Other disadvantages are it is made of soft material of titanium alloy having been reported breakage of nail on repeated bending and straightening while insertion or removal. It is reported in study (J. M. Flynn et al., Journal of Pediatric Orthopedics, Vol. 21, No. 1, 2001 Page, 4-8) that TEN (16) technique requires balancing the forces of the two opposing flexible nails. For the same it requires contour of the nails with an identical gentle curvature, and have to use two different, medial and lateral starting or entry points that are at the same level in the metaphysis (6). It is further reported that to balance it requires same diameter opposing flexible nails to prevent mal-relation of fracture fragments like varus and valgus. It is also reported that for easy removal of nails when required, it is recommended to bend a little distal end to facilitate the application of removal device later on. This bent extra osseous part causes local tissue irritation and pain. Proximal end having flat hockey stick shape (17) bend can cause difficulty in smooth gliding of nail in medullary canal (7) and surgeon has no intraoperative latitude to change the angle of bend according to angle of entry point. Tested on universal testing machine, 3 mm Titanium Elastic Nail (16) shows percentage of elongation only 8% on tensile stress applied, which is the indirect evidence of ductility or elasticity. Test also shows Ultimate Tensile Strength of 1211.14 MPa. Problem of requirement of balancing force of two opposing nails of same diameter having identical curvature with same level two different entry points to prevent mal-relation of fracture fragments is probably due to low flexibility of nails. This nail is made of titanium alloy, which makes its cost high.

Mechanical and clinical studies undertaken by inventor have revealed technical problems and disadvantages with prior art.

DISCLOSURE OF INVENTION

Technical-Problems

1. As mentioned in background of art, a flexible nail to be used for long bones of children requiring side angled entry requires utmost flexibility or elasticity. Prior art nails or pins does not provide required ductility (percentage of elongation on mechanical testing) leading to either difficult entry as in Rush pin (8), straightening of curvatures of bone as in Ender's nail (11), requirement of opposing balancing nails of identical curvature of almost same cross section diameter having two different entry points at same level or otherwise possible mal-relation of fracture fragments as in—TENs (16)

2. Prior art flexible nails are having design of tip of leading end either sharp (9) or slanted sharp (12) or pre-bent flat hockey stick shape (17). These structures many a times make gliding of nail in medullary canal (7) difficult and may cause perforation of super adjacent bone fragment or epiphysis or cause perforation in joint (21) making purpose of surgery ineffective. Sharp (9,12) or flat tip (17) gets lodged at concomitant small undisplaced fracture line in fracture fragment and broaden fracture line, thus causing further malrelation of fracture fragments.

3. Distal ends of prior art nails are having means for removal like hook end (10) as in Rush pin (8) or flattened eye (13) as in Ender's nail (11) or little bend given to extra osseous part or kept 2 cm more out in Titanium Elastic Nail (16), all cause irritation of soft tissue at distal end. There is no means provided for removal of nails, which make removal of nails technically easy at the same time, does not irritate soft tissue.

4. Flexible nails taught in prior art gives stability in medullary canal of long bones at generally three points by its contact with inner surface of medullary canal (7) which is not adequate in unstable fractures where either there are multiple pieces of bone or supporting soft tissues are also disrupted.

5. Flexible nails taught in prior art like Ender's nail (11) is having distal end (13) made flat from round cross section rod and proximal end (17) or leading end of Titanium Elastic Nail (16) is made flat hockey stick shape from round cross section rod. Through the flattening of a round nail cross sectional area, a critical zone of transition (15) will form having a relatively high notch effect, so that with a considerable amount of torque applied at the distal end a plastic deformation or even a shearing off may be the result in this zone.

6. Flexible nails taught in prior art like Ender's nail (11) and Rush pin (8) are made from stainless steel material are stiffer but having low cost, while Titanium Elastic Nails (16) are made from softer titanium alloys with little more flexibility with possibility of breakage and also having high cost. Flexible nails made from titanium-nickel alloys with thermal mechanical memory are costlier than above all.

7. Flexible nails taught in prior art fail in situation where fracture pattern is unstable due to multiple pieces of bone or supporting soft tissues are also disrupted as it does not provide any means for additional rotation stability which is required in such situation.

Technical-Solutions

1. Invention provides straight flexible intramedullary nail (19) of universal length of 50 cm having 15 to 25% of elongation on testing on universal testing machine and ultimate tensile strength of about 600 to 800 MPa (Mega Pascal). Therefore, it provides more ductility, flexibility with adequate strength.

2. Invention provides flexible intramedullary nail (19) with blunt conical pathfinder tip (20) at both ends which glides smoothly in medullary canal (7) of long bones and does not perforate cortex of fracture fragments or will not penetrate epiphysis (3) or joint (21) and does not widen undisplaced fracture line.

3. Invention provides a tool plier-knurler cum cutter (22) for distal end of flexible intramedullary nail (19). Surgeon can cut the nail at a distance of about 1 cm from external surface of bone of entry point, when nose (34) of plier-knurler cum cutter (22) is touching the external surface of bone without bending the nail and at the same time it makes small superficial cuts-knurling type effect (25) on 1 cm of nail protruding from the entry point (24) in bone. On this straight 1 cm part of distal end of nail, which is knurled where, suitable tool for removal at the time of removal, will not slip.

4. Invention provides flexible nails (19) with high flexibility where curvatures (26) in nail can be made at more than one place on nail and in more than one planes, so it gives stability by multiple contact points in medullary canal (7) like loaded spring.

5. Invention provides flexible nails (19) with uniform round cross section diameter in whole length without any transitional zone of weakness (15) or flattening at either end.

6. Invention provides flexible nails (19) made from material like 316 L or 316 LVM stainless steel and cold worked to get more ductility and strength.

7. Invention provides flexible nails (19) with additional adaptable proximal fixation device (27) with or without interlocking screws (28), where adaptable device (27) adapts at proximal end of flexible nails (19), which gives additional rotational stability to proximal fracture fragment at the same time allows minimal axial micro motion at fracture site due to its low axial stiffness.

Advantageous Effects

1. Due to high flexibility, entry of flexible nail (19) in medullary canal (7) becomes easy and it preserves normal anatomic curvatures of long bones. It does not require opposing balancing identical curvatures and same level two different side entries with use of almost equal cross section diameter of flexible nails. It is introduced with single entry point

(24) with lazy "s" shape (29) curvature and "c" shape curvature (30) of any appropriate diameter according to diameter of medullary canal with good elastic stability and without any malrelation of fracture fragments.

2. Prevents injury to super adjacent fracture fragment or epiphysis (3) or concomitant undisplaced fractures. Surgeon can use it from either end and in less height child surgeon can make two nails out of one.

3. Provides means for easy removal of flexible nails (19) at the same time does not irritate soft tissue until removal of nail.

4. Provides more stability in unstable fracture pattern and prevents malrelation of fracture fragments.

5. Provides uniform stability without any plastic deformation or shearing off at either end with torque applied on distal end.

6. Provides high flexibility with strength at the same time with lower cost than nails made from material like titanium alloys or shape memory alloys.

7. Provides additional rotational stability in unstable fracture pattern or where supporting soft tissues are disrupted and prevents mal-relation of fracture fragments till union of fractures. It allows early weight bearing by patient and also stimulates callus formation at fracture site by axial micro motion.

DESCRIPTION OF DRAWINGS

FIG. 3A shows side view of Upper end of Rush Pin showing pin bent like hook.

FIG. 3B shows side view of Lower end of Rush Pin showing sharp bent tip.

FIG. 3C shows front inside view of Ender's Nail showing lower end having flat with eye and critical zone of transition.

FIG. 3D shows side view of Ender's Nail showing lower end flat with eye and critical zone of transition and upper end with predefined curvatures.

FIG. 3E shows side view of Titanium Elastic Nail showing upper end bent like hockey stick shape and flat with critical zone of transition.

FIG. 4A shows elevation of proposed Flexible Nail implant showing it straight before insertion in to medullary canal.

FIGS. 4B, 4C and 4D shows side view of proposed Flexible Nail showing different curvatures like lazy "s" shapes and "c" shape when inserted into medullary canal.

FIG. 6A shows Plier-Knurler cum Cutter showing its jaws, nose, knurler part of 1 cm length, cutting part and handle part.

FIG. 6B shows enlarged view of distal end of proposed nail showing superficial small cuts on the surface of distal most 1 cm of nail-knurling type effect to have easy grip at the time of removal of nail.

FIG. 12 B shows cut section of Proximal Fixation Device at the line XY passing through holes for interlocking screw showing grooves equally spaced apart at four corners of solid shaft part and cut on non grooved part for interlocking screw.

MODE FOR INVENTION

Figure 1:
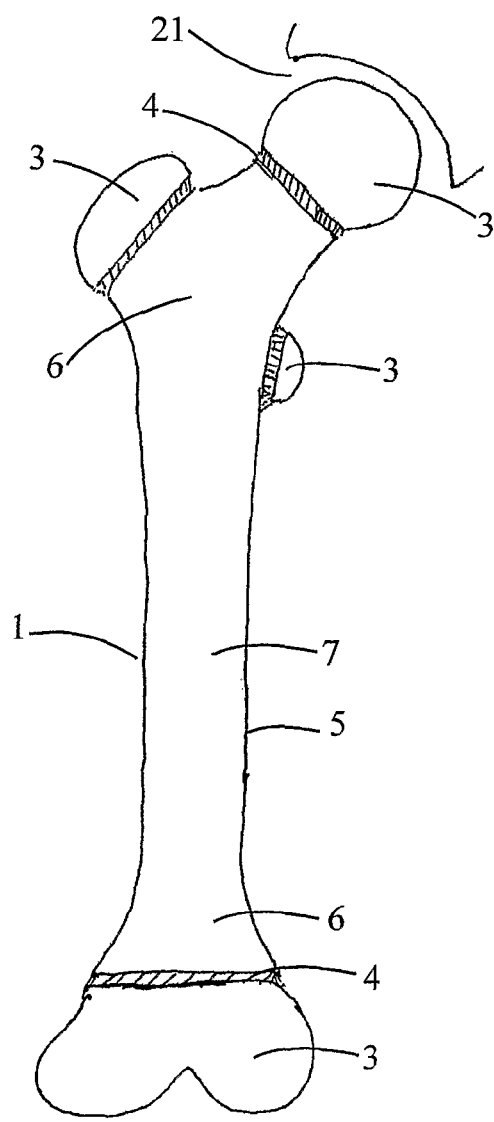
FIG. 1 shows front view of normal human child's femur bone showing Epiphysis, metaphysic and diaphysis and growth plate.
Figure 2:
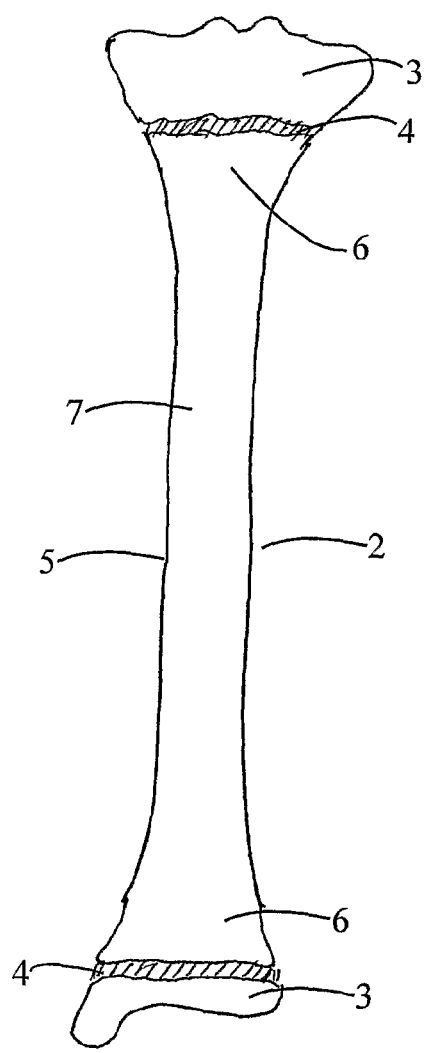
FIG. 2 shows front view of normal human child's tibia bone showing Epiphysis, metaphysis and diaphysis and growth plate.
Figure 5A:
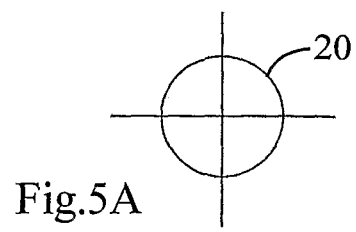
FIGS. 5A and 5B shows enlarged view of conical pathfinder tip and plan of nail respectively.
Figure 5B:
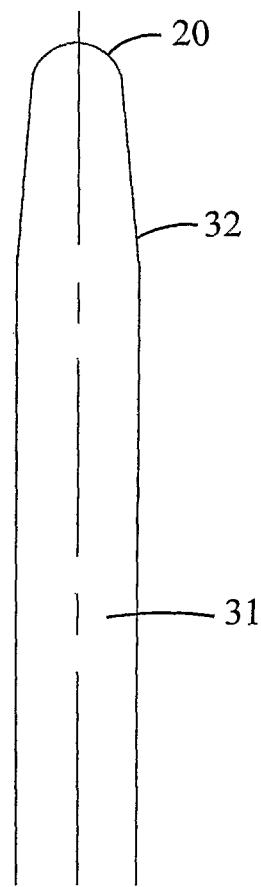

As shown in FIG. 4A Flexible Intramedullary Nail is straight having universal length preferably of 50 cm, is having identical proximal end (32) and distal end (23) and part in between two ends is shaft (31). As shown in FIGS. 5A and 5B, proximal end (32) and Distal end (23) is having tip (20), which is round in cross section and conical round at end. Conical part is having less cross section diameter than shaft part (31). Purpose of having universal length is to give surgeon intraoperative latitude to have exact length even in fractions of centimeter, so that upper end do not do injury to epiphysis, at the same time lower end does not irritate soft tissue. Purpose of conical round pathfinder tip (20) is to have very easy gliding of flexible nail (19) in medullary canal (7) and will not penetrate super adjacent fracture fragment or joint (21). Conical pathfinder tip (20) is not stuck in concomitant undisplaced fractures. Flexible nail (19) can be made from material like 316 L or 316 LVM stainless steel to get strength at the same time to reduce cost. It is processed by cold method to get higher ductility than titanium and high ultimate tensile strength. It is made by drawing from ingot. FIG. 4B, 4C 4D, 7A, 7B, 8A, 8B, 9, 10 shows its flexibility when inserted in medullary canal (7). Final product Flexible Nail (19) should have 15-25% of elongation and about 600 to 800 MPa (Mega Pascal) ultimate strength on testing done by universal testing machine. The nails are the chief stress bearing members of fixation and they must be stiff without being rigid. They must be resilient or flexible to return to their original position when off-loaded axially. In medullary canal (7) when Flexible nails (19) of sufficient in number and diameter are introduced from single distal or proximal entry point (24) generally taking lazy "S" shape (29) or "C" shape (30) in medullary canal (7) having multiple contact points of fixation. On weight bearing by patient on walking these curves (26) of flexible nails (19) changes, but returns to original shape curves on offloading. Shaft (31) part of flexible nail is round in cross section ranging from 2 mm to 4 mm diameter. Since as previously explained, a plurality of nails may be employed in one operation; the actual effective diameter is to be calculated and may, in fact, vary in accordance with the preference of the surgeon. One surgeon might prefer to use a single nail of greater diameter while another might choose to use two or more of lesser diameter or combinations of different diameter. Due to its flexibility, it gives total freedom to surgeon to choose single entry point (24) and to have different combinations of diameter or curvatures (26).

A plier-knurler cum cutter (22) as shown in FIG. 6A comprises jaws (33) having nose (34), knurler surface (35) of 1 cm length, a cutting part (36) and handle part (37). After final insertion of flexible nail (19), knurler part (35) holds the 1 cm of nail while nose (34) touching the external surface of bone of entry point (24). On pressing by handle (37) knurler part (35) makes small superficial cuts on the surface of held 1 cm of flexible nail, at the same time cutting part (36) cuts the nail (19) leaving only 1 cm protruding from entry point. Finally, as shown in FIG. 6B it gives knurling type superficial cuts (25) on nail (19) making it technically easy to remove at the time of removal at the same time as only 1 cm of nail (19) is protruding outside the entry point, it will not irritate soft tissue and will not cause pain to patient.

Figures 11A, 12A:
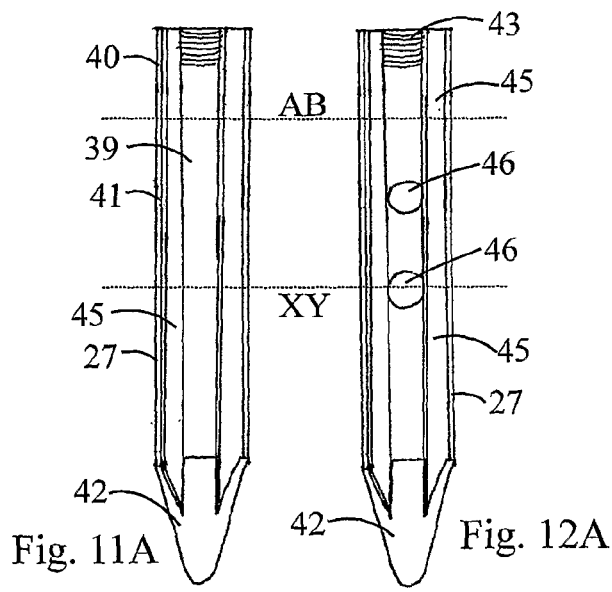
FIG. 11A shows elevation of Proximal Fixation Device without holes for interlocking screws showing upper part or head having internal threads, middle part or shaft having longitudinal grooves on surface and tapered round distal end or tail.
Figure 11B:
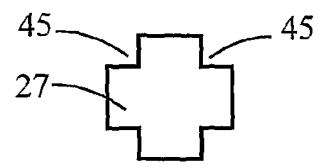
FIG. 11B shows cut section of Proximal Fixation Device at the line AB showing grooves equally spaced apart at four corners of solid shaft part.
Figure 12B:
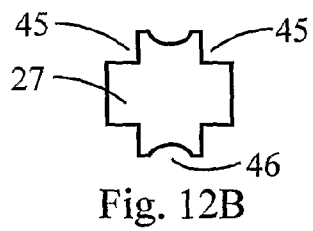
FIG. 12 A shows elevation of Proximal Fixation Device with holes in shaft part for interlocking screws showing upper internally threaded end, middle part or shaft having longitudinal grooves on surface and tapered round distal end or tail.
Figure 14:
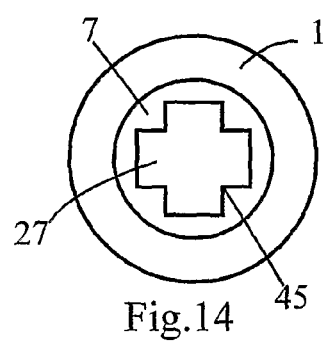
FIG. 14 shows cross section of femur bone with Proximal fixation device inserted in medullary canal showing medullary canal and cut section of proximal fixation device showing grooves at periphery for flexible nails.
Figure 15:
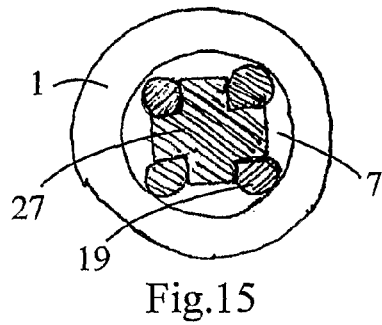
FIG. 15 shows cross section of femur bone with Proximal fixation device inserted in medullary canal and flexible nails passed in peripheral grooves showing medullary canal and cut section of proximal fixation device showing grooves filled with round flexible nails.
Figure 16:
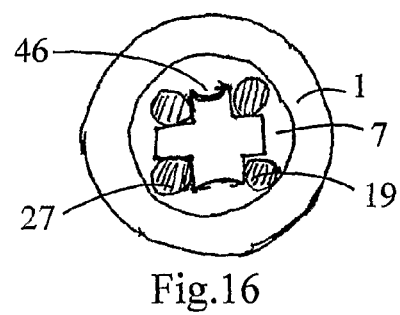
FIG. 16 shows cross section of femur bone a the level of interlocking screw with Proximal fixation device inserted in medullary canal and flexible nails passed in peripheral grooves showing medullary canal and cut section of proximal fixation device showing grooves filled with round flexible nails and cut in non grooved shaft for interlocking screw.

Optional Proximal Fixation Device (27) with or without interlocking screws (28) and End cap (38) are be used with plurality of above described flexible nails (19). As shown in FIG. 11A, 12A, preferred proximal fixation device (27) comprises of Proximal or Head part (40), Intermediate or shaft part (41) and distal or tail part (42). Proximal fixation device is solid intramedullary rod (39) made from suitable stainless steel or other compatible material to be passed in medullary canal (7) of suitable diameter where cross section diameter is different at head part (40) and tail part (42) part. Head part (40) is having internal threads (43) for temporary adaptation of suitable targeting device for interlocking option and for permanent adaptation of externally threaded part (44) of end cap (38). As shown in FIG. 11A, 11B, 12A, 12B, Head (40) and Shaft (41) is having 2-4 grooves (45) extending whole length equally spaced from each other around periphery. These grooves (45) serve to guide the flexible nails (19) into place on insertion and to hold them in an approximately parallel position to support the fracture during healing. The longitudinal grooves (45) can have various cross-section forms, but must give lateral support to the pins and have a depth of less than one nail diameter. This shallow depth ensures that the sides of the nails will project radialy out from the surface of proximal fixation device (27) as longitudinal ridges. To have easy insertion of the proximal fixation device (27) into the medullary canal (7) of a bone, the distal end or tail (42) of the device is tapered to a blunt rounded point. Proximal fixation device (27) is 9-13 mm. in diameter with two to four longitudinal grooves (45) each about 3 mm. wide and about 1.2 mm. deep. As shown in FIG. 12 A, when proximal fixation device (27) with holes (46) for interlocking screws (28) is preferred, number of grooves (45) will be at least two. However, proximal fixation devices will range from about 9-13 mm. Diameter and about 65-220 mm. in length with different number of grooves (45) in different combinations according to requirement and choice of surgeon. As shown in FIGS. 14,15 and 16 cross section of proximal fixation device (27) as if it assembled in medullary canal (7) of femur (1) bone without flexible nails (19), with four flexible nails (19) and with flexible pins (19) and hole (46) for interlocking screw (28) successively. Optionally as shown in FIGS. 12A and 12 B, Proximal fixation device (27) may have plurality of through hole transversely or obliquely placed in shaft (41) part for interlocking screw (28). Proximal fixation device (27) in use with combination with plurality of flexible nails (19) gives increased stability of the fracture during healing. The stress bearing nails are held at the periphery of the medullary canal (7), where they can best resist torsional (twisting) and flexural loads with optional interlocking screw (28). It increases stability at the same time preserves springiness of flexible nails (19) without hampering endosteal vascularity of fracture fragment, as insertion of flexible nails does not require broaching of canal. It gives sufficient control of transverse, torsion and flexural stress to prevent displacement of fracture ends, but not such complete control as to eliminate those stresses below a level beneficial to healing. The proximal fixation device (27) with multiple flexible nails (19) of this invention has relatively low resistance to axial movement in the bone. Therefore, it allows some axial impaction of the fracture, which also aids the healing process.

Figure 13:
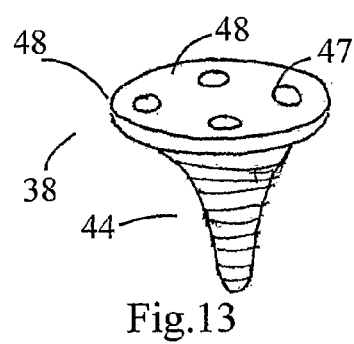
FIG. 13 shows elevation of end cap showing threaded part adaptable to threaded part of proximal fixation device and head part with holes for holding flexible nails.

As shown in FIG. 13 End cap (38) comprises of Head part (47) and Shaft or threaded part (44). Head part (47) is having generally round cross sectional diameter larger than shaft part (44) and is having plurality of holes (48) for adaptation of ends of flexible nails (19) to be hooked (53) with it. Shaft part (44) is having small diameter externally threaded portion to be have final attachment with internally threaded part (43) of proximal fixation device (27). Purpose of end cap is to give proximal anchor and to retain hooked ends (53) of multiple flexible nails (19) to add stability.

BEST MODE OF INVENTION

Figure 7A:
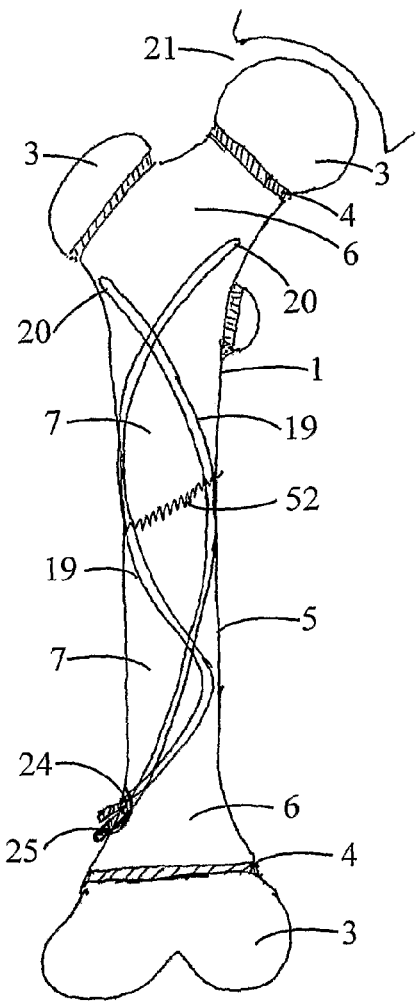
FIGS. 7A and 7B shows schematic of child's femur bone showing proposed flexible nails inserted in medullary canal by single entry point from distal and proximal end of bone respectively having multiple points of contact in medullary canal.

In case of fracture of shaft femur in child the proposed implant is implemented in the manner given below:

First of all patient is positioned on fracture table and anatomical reduction of shaft femur fracture is done and confirmed with imaging device in both planes known to those ordinarily skilled in art. Local parts are prepared and draped to get sterile field as per usual manner known to person skilled in art. Short length incision is made on lateral aspect of lower thigh. An angled appropriate hole is made in lateral cortex of femur 2 cm above the epiphysis (3) as known to person skilled in art. Flexible nail (19) of appropriate diameter is mounted on suitable T-handle tool known to those skilled in art. A slight bend is given at the end of flexible nail (19) to facilitate entry in the medullary canal (7) and desired curvatures (26) are given gently. Now the nail (19) is inserted in medullary canal (7) under observation with imaging device by gentle rotatary and push movement. It glides very smoothly in medullary canal. Now it is passed to opposite fragment over fracture zone (52). On gradual passing to super adjacent fragment it automatically improves relation of fracture fragments. Now it is hammered to final position to dense metaphyseal (6) bone. After final fixation, 1 cm of nail is kept out with knurling effect (25) with the help of plier-knurler cum cutter (22) to have a grip of nail at the time of removal at the same time not irritating soft tissues at lower end of thigh. Successive flexible nails (19) with different curvature (26) are inserted in medullary canal (7) from same lateral entry hole at lower thigh till adequate stability is achieved as shown in FIG. 7A.

Figure 7B:
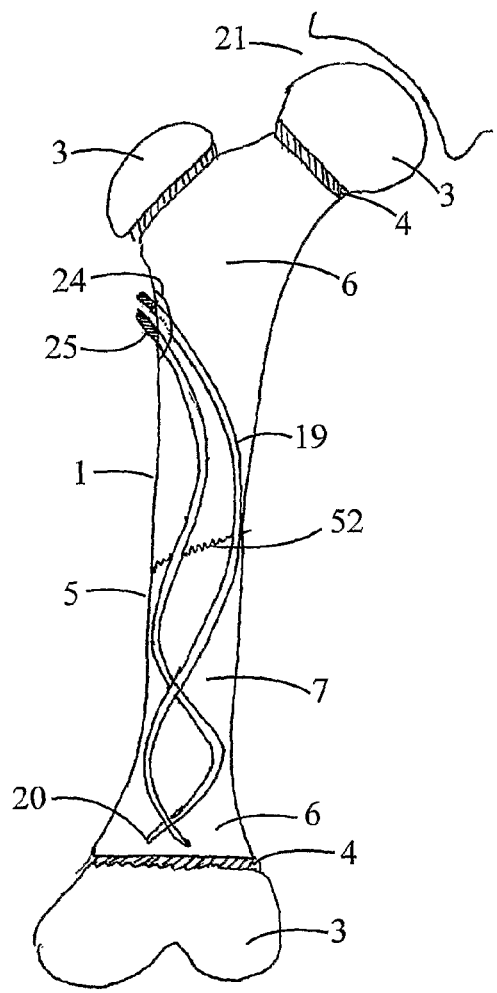
Figure 8A:
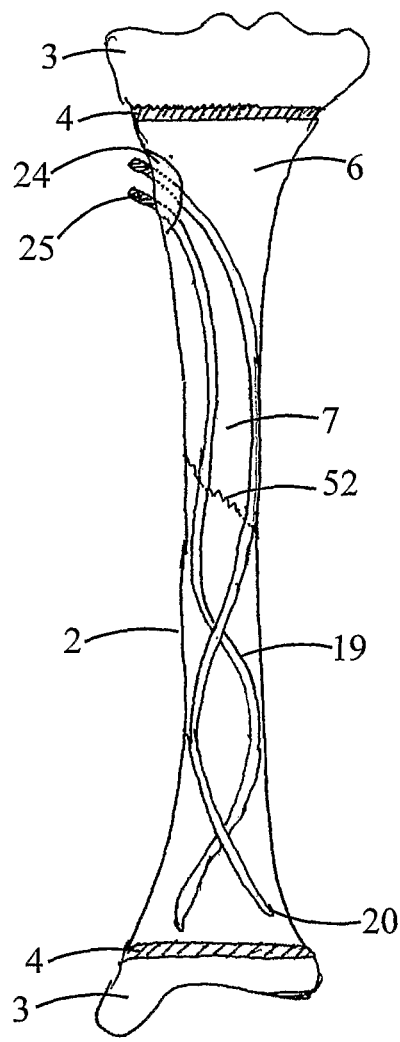
FIGS. 8A and 8B shows schematic of child's tibia bone showing proposed flexible nails inserted in medullary canal by single entry point from proximal and distal end of bone respectively having multiple points of contact in medullary canal.
Figure 8B:
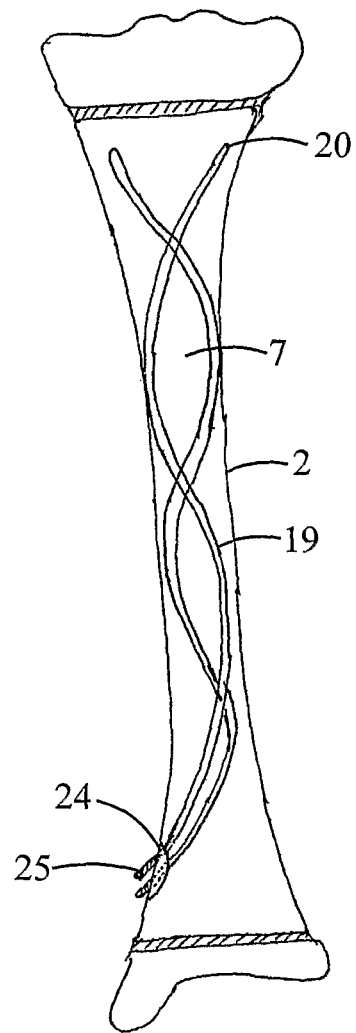
Figure 9:
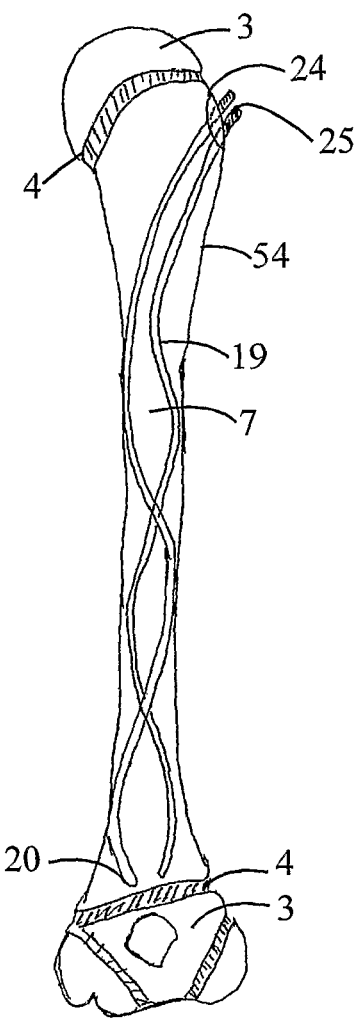
FIG. 9 shows schematic of child's humerus bone showing proposed flexible nails inserted in medullary canal by single entry point from proximal end of bone having multiple points of contact in medullary canal.
Figure 10:
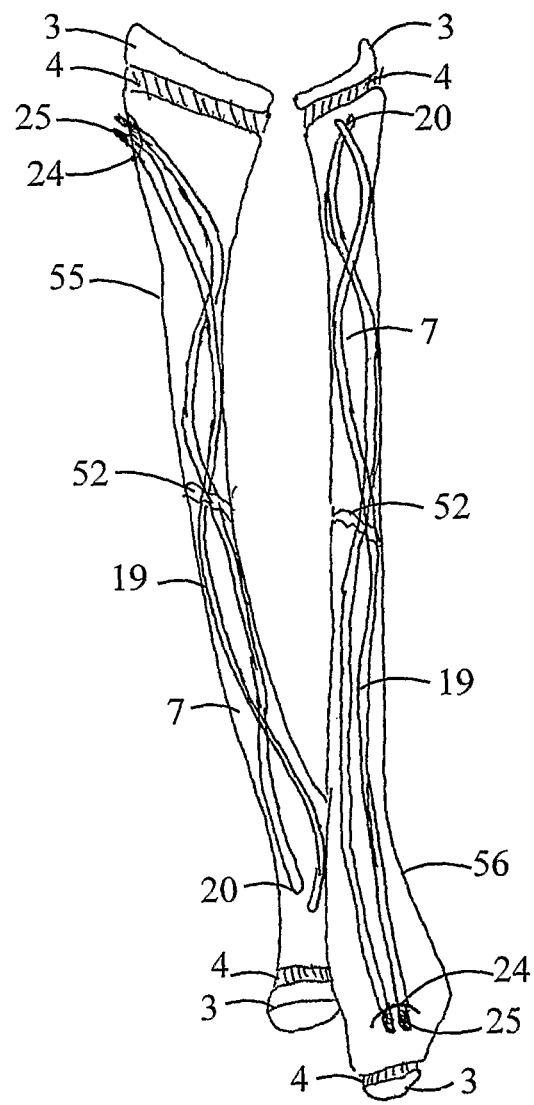
FIG. 10 shows schematic of child's radius and ulna bone showing proposed flexible nails inserted in medullary canal by single entry point from proximal end in ulna and from distal end in radius having multiple points of contact in medullary canal.

As shown in FIG. 7B, entry site may be chosen by surgeon at upper end of thigh for fracture of femur (1) bone. As shown in FIG. 8A and FIG. 8B fractures of Tibia (2) bone can be treated in same manner taking either proximal or distal entry point respectively. As shown in FIG. 9 fractures of Humerus (54) bone can be treated in same manner with flexible nails. As shown in FIG. 10 fractures of Forearm bones radius (55) and ulna (56) can be treated in same manner with flexible nails (19).

In case of fracture of shaft femur (1) in adult or adolescent, the proposed implant is implemented with proximal fixation device (27) with or without interlocking screws (28) in the manner given below.

Figure 17:
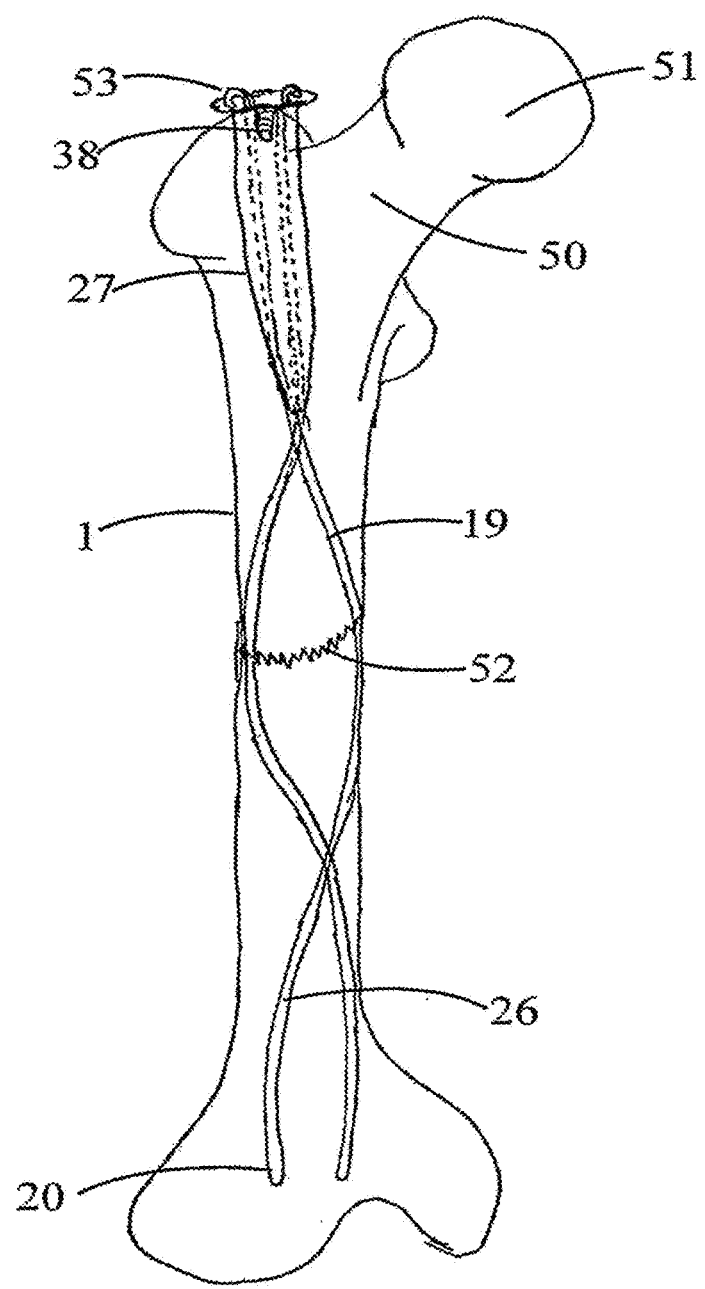
FIG. 17 shows schematic of front view of adult human femur bone with fracture in shaft of femur showing Proximal fixation device without holes for interlocking screw and flexible nails passed through grooves in proximal fixation device, flexible nails have crossed fracture zone, and end cap holding hooked cut ends of flexible nail.
Figure 18:
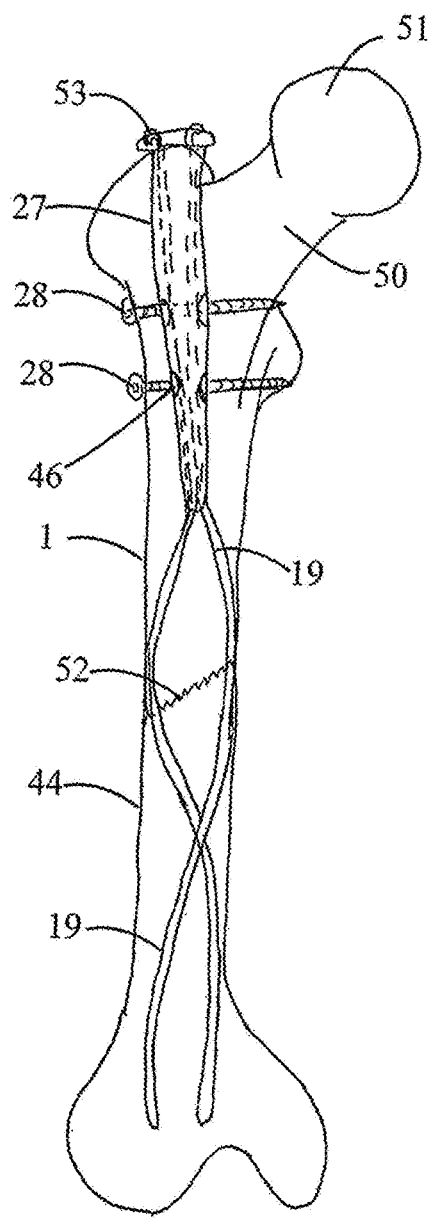
FIG. 18 shows schematic of front view of adult human femur bone with fracture in shaft of femur showing Proximal fixation device with holes for interlocking screw, flexible nails passed through grooves in proximal fixation device and flexible nails have crossed fracture zone and interlocking screw are placed transversely in shaft of femur and end cap holding hooked cut ends of flexible nail.
Figure 19:
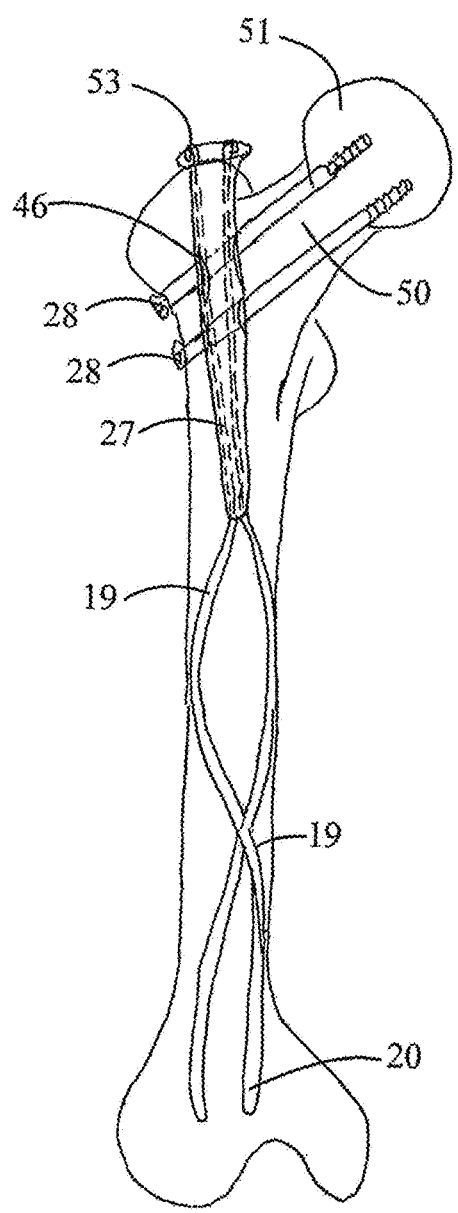
FIG. 19 shows schematic of front view of adult human femur bone with fracture in shaft of femur showing Proximal fixation device with holes for interlocking screw and end cap holding flexible nails passed through grooves in proximal fixation device and flexible nails have crossed fracture zone and interlocking screw are placed obliquely in head and neck of femur bone.

First of all patient is positioned on fracture table and anatomical reduction of shaft femur (1) fracture is done and confirmed with imaging device in both planes known to those ordinarily skilled in art. Local parts are prepared and draped to get sterile field as per usual manner known to person skilled in art. An angled appropriate hole is made at upper end of femur and extended to medullary canal, (7) by proper reaming up to 65 to 220 mm as known to person skilled in art. Now a proximal fixation device (27) is mounted on targeting device. Keeping tail (42) end as leading end proximal fixation device (27) is inserted in to medullary canal (7) by gentle push and rotatary movement. Now flexible nail (19) is inserted through one of the longitudinal grooves (45) around periphery of proximal fixation device (27), pushed down, and rotated to desired position in lower metaphysis (6) of femur (1). Same procedure is repeated by introducing another flexible nail (19) having different direction of rotation passing through another groove (45). Now after final insertion flexible nails (19), protruding out nails are cut. Now through the holes (48) in end cap (38) cut ends of flexible nails (19) are passed and threaded part (44) of end cap is adapted well with internally threaded part (43) of head (40) of proximal fixation device (27). Cut ends of Nails (19) bent like hook (53), finally hammered to rest upon, and hooked to the periphery of head part (47) of end cap (38) as shown in FIG. 17. In cases where additional rotational stability is required, fixation device with holes (46) in shaft part (41) is selected and interlocking screws (28) are passed transversely as shown in FIG. 18 or obliquely in to head (51) and neck (50) of femur (1) as shown in FIG. 19.

Postoperatively patients are allowed to have pain oriented weight bearing. Initially implant takes full load of different forces acting on femur and it reacts effectively by allowing limited axial collapse of fracture gap leading to early bone to bone contact and healing. In this way, gradually the implant diverts the above said load to fractured femur bone stimulating healing of femur bone without any postoperative setbacks.

Those of ordinary skill in the art will further understand and appreciate from the totality of the foregoing disclosure, that the various alternative features and components shown and discussed in conjunction with FIG. 1 through 19, may be practiced in accordance with various installation and withdrawal methodologies. All of which combinations are intended to come within the spirit and the scope of the present invention, without rediscussion thereof. Such alternative methodologies are intended to include the use of different flexible nail and proximal fixation device embodiments practiced in accordance with the invention. It should be further understood by those of ordinary skill in the art that the foregoing presently preferred embodiments are exemplary only, and that the attendant description thereof is likewise by way of words of example rather than words of limitation. Their use does not preclude inclusion of such modifications, variations, and/or additions to the present invention (either apparatus or methodology) as would be readily apparent to one of ordinary skill in the art, the scope of the present invention being set forth in the appended claims.

INDUSTRIAL APPLICABILITY

An orthopedic implant of Flexible Nail alone or in combination with Proximal Fixation Device with or without interlocking screws of the present invention is biomechanically a superior method of treating a wide range of fractures of shaft of long bones in children or adults. It can be used for reconstruction of the shaft of long bones, allograft reconstruction of the shaft of long bones after tumor resection, and leg lengthening. Those skilled in the art will recognize other uses.

What is claimed is:

1. An orthopedic implant consisting of:
   a straight single flexible nail, wherein said nail comprising:
   a universal length;
   a first free end consisting of a first pathfinder conical tip;
   a second free end consisting of a second pathfinder conical tip; and
   a shaft defining a long axis of said nail,
   wherein said shaft and said first free end and said second free end are capable of having a plurality of curvatures at a plurality of planes along said long axis, thereby allowing said nail to fix, reposition and maintain relation of fracture fragments at a plurality of contact points of fixation inside a medullary canal and
   wherein said nail has a structure of 15-25% elongation on tensile stress and an ultimate tensile strength of about 600-800 MPa.

2. An orthopedic implant of claim 1 wherein said flexible nail is characterized having made from material comprising one of 316 L (low carbon) or 316 LVM (low carbon vacuum melted) stainless steel or other biocompatible material.

3. An orthopedic implant of claim 1, wherein said first free end and said second free end are identical.

4. An orthopedic implant of claim 1, wherein said shaft has a first cross section diameter d1, wherein each of said first free end and said second free end has a second cross section diameter d2 and a third cross section diameter d3, wherein each of said first pathfinder conical tip and second pathfinder conical tip has a fourth cross section diameter d4, wherein d4<d3, d3<d2, d2<d1.

5. An orthopedic implant of claim 1, wherein said nail has a uniform surface along whole length.

6. An orthopedic implant of claim 1, wherein after final placement of said nail, a non-leading end of said nail has a structure capable of being cut at a distance substantially equal to 1 cm from an entry and said distance of a cut end has a structure capable of being roughened.

7. A plier cum knurler cum cutter to hold, to cute and to make a surface rough of a cut end of a straight single flexible nail, wherein said nail comprising:
   a straight single flexible nail, wherein said nail comprising:
   a universal length;
   a first free end consisting of a first pathfinder conical tip;
   a second free end consisting of a second pathfinder conical tip; and
   a shaft defining a long axis of said nail,
   wherein said shaft and said first free end and said second free end are capable of having a plurality of curvatures at a plurality of planes along said long axis, thereby allowing said nail to fix, reposition and maintain relation of fracture fragments at a plurality of contact points of fixation inside a medullary canal and
   wherein said nail has a structure of 15-25% elongation on tensile stress and an ultimate tensile strength of about 600-800 MPa
said plier cum knurler cum cutter comprising:
   a knurler part and a cutting part, wherein on operation of said plier cum knurler cum cutter, said cutting part has a structure capable to cut said flexible nail at a distance substantially equal to 1 centimeter from an entry point and said knurler has a structure capable to make the surface of said cut end of said flexible nail rough for easy removal later on.

8. A method of treating a bone having a medullary canal fractured into a plurality of fragments using at least one intramedullary flexible nail and providing means for removal of said flexible nail without irritating soft tissue comprising steps of:
   a) making an entry in said bone leading to said medullary canal;
   b) pushing said flexible nail through said entry into said medullary canal irrespective to shape of said medullary canal, said flexible nail consisting of:
   a straight single flexible nail comprising:
   a universal length;
   a first free end consisting of a first pathfinder conical tip;
   a second free end consisting of a second pathfinder conical tip; and
   a shaft defining a long axis of said nail,
   wherein said shaft and said first free end and said second free end are capable of having a plurality of curvatures at a plurality of planes along said long axis, thereby allowing said nail to fix, reposition and maintain relation of fracture fragments at a plurality of contact points of fixation inside a medullary canal and
   wherein said nail has a structure of 15-25% elongation on tensile stress and an ultimate tensile strength of about 600-800 MPa; and
   c) after final pushing, a non-leading end is cut substantially keeping 1 cm outside said entry to prevent soft tissue irritation and a surface of a cut end of said flexible nail is roughened to have grip for easy removal of said flexible nail later on.

\* \* \* \* \*